United States Patent [19]
Ecker et al.

[11] Patent Number: 5,674,701
[45] Date of Patent: Oct. 7, 1997

[54] METHOD OF IDENTIFYING PLANT PATHOGEN TOLERANCE

[75] Inventors: Joseph R. Ecker, Erial, N.J.; Brian J. Staskawicz, Castro Valley; Andrew F. Bent, Piedmont, both of Calif.; Roger W. Innes, Bloomington, Ind.

[73] Assignees: The Trustees of the University of Pennsylvania, Philadelphia, Pa.; The Regents of the University of California, Berkeley, Calif.

[21] Appl. No.: 171,207

[22] Filed: Dec. 21, 1993

Related U.S. Application Data

[63] Continuation of Ser. No. 899,262, Jun. 16, 1992, abandoned.
[51] Int. Cl.$^6$ ............... C12Q 1/18; A01H 5/00
[52] U.S. Cl. ............ 435/32; 435/7.2; 800/200; 800/DIG. 23; 800/DIG. 15; 47/58
[58] Field of Search ............ 899/262; 47/58.07; 800/200, DIG. 15, DIG. 23; 435/7.2, 32

[56] References Cited

U.S. PATENT DOCUMENTS

| | | | |
|---|---|---|---|
| 4,374,661 | 2/1983 | Fritz et al. | 71/86 |
| 5,084,082 | 1/1992 | Sebastian | 504/212 |

OTHER PUBLICATIONS

Boller T. Ethylene in Pathogenesis and Disease Resistance Chapter 6, *The Plant Hormone Ethylene*, eds., Mattoo, Autark., and Suttle, Jeffrey C., 1991, CRC Press, Inc.

Debener et al. Identification and Molecular Mapping of a Single Arabidopsis–thaliana Locus Determining Resistance to a Phytopathogenic Pseudomonas–syringae Isolate *The Plant Jour.* 1:289–302 1991.

Swanson et al., Cloned Avirulence Gene of Xanthomonas campestris pv. vesicatoria Complements Spontaneous Race–Change Mutants *Mol Plant–Microbe Interact.* 1:5–9 1988.

Whalen et al., Identification of Pseudomonas syringae Pathogens of Arabidopsis and a Bacetrial Locus Determining Avirulence on Both Arabidopsis and Soybean *The Plant Cell* 3:49–59 1991.

Dong et al., Induction of Arabidopsis Defense Genes by Virlent and Avirulent Pseudomonas syringae Strains and by a cCloned Avirulence Gene *The Plant Cell* 3:61–72 1991.

Ecker et al., Ethylene Regulation of Plant Defense Genes *Molecular Biology of Plant Growth Control* 133–143 1987.

Staskawicz et al., Molecular Characterization of Cloned Avirulence Genes from Race 0 and Race 1 of Pseudomonas syringae pv. glycinea *J. Bacteriol.* 169:5789–5794 1987.

Tamaki et al., Characterization and Expression of Two Avirulence Genes Cloned from Pseudomonas syringae pv. glycinea *J. Bacteriol* 170:4846–4854 1988.

Huynh et al., Bacterial Blight of Soybean: Regulation of a Pathogen Gene Determining Host Cultivar Spcecificity *Science* 245:1374–1377 1989.

Ferguson et al.,Stimulation of Ethylene Production in Bean Leaf Discs by the Pseudomonad Phytotoin Coronatine *Plant Physiol.* 77:969–973 1985.

Ecker et al., Plant Defense Genes are Regulated by Ethylene *Proc. Natl. Acad. Sci. USA* 84:5202–5206 Aug. 1987.

Bleecker et al., Insensitivity to Ethylene Conferred by A Dominant Mutation in Arabidopsis thaliana *Science* 241:1086–1089 1990.

King, E.O. et al., Two Simple Media for the Demonstration of Pyocyain and Fluorescin *J. Lab. Clin. Med.* 44:301–307 1954.

Daniels, M.J. et al, Isolation of Mutants of Xanthomonas campestris pv. campestris Showing Altered Pathogenicity *J. Gen. Microbiol.* 130:2447–2455 1984.

Oeller et al., Reversible Inhibition of Tomato Fruit Senescence by Antisense RNA *Reports* 437 Oct. 1991.

Prentki and Krisch, In Vitro Insertional Mutagenesis with a Selectable DNA Fragment *Gene* 29:303–313 1984.

Guzman et al., Exploiting the Triple Response of Arabidopsis to Identify Ethylene–Related Mutants *The Plant Cell* 2:513–523 Jun. 1990.

Ecker et al, Inhibition of Gene Expression in Plant Cells by Expression of Antisense RNA *Proc. Natl. Acad. Sci. USA* 83:5372–5376 Aug. 1986.

Bent et al., Disease Development in Ethylene–Insensitive Arabidopsis tahliana Infected with Virulent and Avirulent Pseudomonas and Xanthomonas Pathogens *Mol. Plant–Microbe Inter.* 5:372–378 1992.

Mussell, H. Tolerance to Disease *Plant Disease* 5:39–51 1980.

Agrios, G.N., Plant Pathology *Acad Press* 3rd. Ed. 125–129 1988.

Myers et al. (Nov.–Dec. 1991) Crop Science vol. 31: 1710 1991.

Bleecker, et al (26 Aug. 1988) Science 241: 1086–1089.

Guzman et al (Jun. 1990) The Plant Cell 2: 513–523.

Wendland, et al (1988) Zeitschrift fuer Plonzenkrank–heiten und Planyenschutz 95 (2): 113–123. English Abstract.

Estelle,et al (Apr. 1986) Trends in Genetics 2: 89–93.

*Primary Examiner*—Che S. Chereskin
*Attorney, Agent, or Firm*—Woodcock Washburn Kurtz Mackiewicz & Norris

[57] ABSTRACT

A process for identifying a plant having disease tolerance comprising administering to a plant an inhibitory amount of ethylene and screening for ethylene insensitivity, thereby identifying a disease tolerant plant, is described. Plants identified by the foregoing process are also described.

21 Claims, 5 Drawing Sheets

METHOD OF IDENTIFYING PLANT PATHOGEN TOLERANCE

This is a continuation, of application Ser. No. 899,262, filed Jun. 16, 1992, now abandoned.

REFERENCE TO GOVERNMENT GRANTS

This work was supported in part by research grants from the National Institutes of Health, grant number GM-38894, the Department of Energy, grant number DE-FG03-88ER13917 and National Science Foundation grants. The United States Government may have certain rights in this invention.

BACKGROUND OF THE INVENTION

As in animal systems, response of plants to disease not only involves static processes, but also involves inducible defense mechanisms. One of the earliest detectable event to occur during plant-pathogen interaction is a rapid increase in ethylene biosynthesis. Ethylene, a gaseous plant hormone, is involved in the regulation of a number of plant processes ranging from growth and development to fruit ripening. Ethylene biosynthesis, in response to pathogen invasion, correlates with increased defense mechanisms, chlorosis, senescence and abscission. The molecular mechanisms underlying operation of ethylene action, however, are unknown. Nonetheless, ethylene produced in response to biological stress is known to regulate the rate of transcription of specific plant genes. A variety of biological stresses can induce ethylene production in plants including wounding, bacterial, viral or fungal infection as can treatment with elicitors, such as glycopeptide elicitor preparations (prepared by chemical extraction from fungal pathogen cells). Researchers have found, for example, that treatment of plants with ethylene generally increases the level of many pathogen-inducible "defense proteins", including β-1,3-glucanase, chitinase, L-phenylalanine ammonia lyase, and hydroxyproline-rich glycoproteins. The genes for these proteins can be transcriptionally activated by ethylene and their expression can be blocked by inhibitors of ethylene biosynthesis. Researchers have also characterized a normal plant response to the production or administration of ethylene, as a so-called "triple response". The triple response involves inhibition of root and stem elongation, radial swelling of the stem and absence of normal geotropic response (diageotropism).

Regardless of the molecular mechanisms involved, the normal ethylene response of a plant to pathogen invasion has been thought to have a cause and effect relationship in the ability of a plant to fight off plant pathogens. Plants insensitive in any fashion to ethylene were believed to be incapable of eliciting a proper defense response to pathogen invasion, and thus unable to initiate proper defense mechanisms. As such, ethylene insensitive plants were thought to be less disease tolerant.

The induction of disease responses in plants requires recognition of pathogens or pathogen-induced symptoms. In a large number of plant-pathogen interactions, successful resistance is observed when the plant has a resistance gene with functional specificity for pathogens that carry a particular avirulence gene. If the plant and pathogen carry resistance and avirulence genes with matched specificity, disease spread is curtailed and a hypersensitive response involving localized cell death and physical isolation of the pathogen typically occurs. In the absence of matched resistance and avirulence genes, colonization and tissue damage proceed past the site of initial infection and disease is observed.

Whalen et al. in "Identification of *Pseudomonas syringae* Pathogens of Arabidopsis and a Bacterial Locus Determining Avirulence on Both Arabidopsis and Soybean", *The Plant Cell*, Vol. 3, pp. 49–59 (1991), Dong et al. in "Induction of Arabidopsis Defense Genes by Virulent and Avirulent *Pseudomonas syringae* Strains and by a Cloned Avirulence Gene", *The Plant Cell*, Vol. 3, pp. 61–72 (1991) and Debener et al. in "Identification and Molecular Mapping of a Single *Arabidopsis thaliana* Locus Determining Resistance to a Phytopathogenic *Pseudomonas syringae* Isolate", *The Plant Journal*, Vol. 1, pp. 289–302 (1991) have identified the interaction between *Arabidopsis thaliana* and *Pseudomonas syringae* bacteria. *P. syringae* pv. *tomato* (Pst) strains are pathogenic on Arabidopsis. A single bacterial gene, avrRpt2, was isolated that controls pathogen avirulence on specific Arabidopsis host genotype Col-0.

A survey of previously cloned avirulence genes revealed that the well-characterized avrB locus from *Pseudomonas syringae* pv. *glycinea* converted virulent Pst strains to avirulence on Arabidopsis ecotype Col-0, see Staskawicz et al., "Molecular Characterization of Cloned Avirulence Genes from Race 0 and Race 1 of *Pseudomonas syringae* pv. *glycinea*", *J. Bacteriol.*, Vol. 169, p. 5789 (1987), Tamaki et al., "Characterization and Expression of Two Avirulence Genes Cloned from *Pseudomonas syringae* pv. *glycinea*", *J. Bacteriol*, Vol. 170, p. 4846 (1988) and Huynh et al., "Bacterial Blight of Soybean: Regulation of a Pathogen Gene Determining Host Cultivar Specificity", *Science*, Vol. 245, p. 1374 (1989). Debener et al., "Identification and Molecular Mapping of a Single *Arabidopsis thaliana* Locus Determining Resistance to a Phytopathogenic *Pseudomonas syringae* Isolate", *The Plant Journal*, Vol. 1, pp. 289–302 (1991) have isolated avrRpm1 from *Pseudomonas syringae* pv. *maculicola* and has determined that this locus causes avirulence in infections of Arabidopsis ecotype Col-0.

A better understanding of plant pathogen tolerance is needed. Also needed is the development of methods for improving the tolerance of plants to pathogens, as well as the development of easy and efficient methods for identifying pathogen tolerant plants.

The present invention addresses some of these very important needs through an approach which runs contrary to prevailing hypotheses on the relationship between ethylene response and pathogen invasion in plants. Surprisingly, it has been found that plants which have decreased ethylene sensitivity or are insensitive to ethylene have greater disease tolerance. Thus, the present invention is directed to methods for the identification of plants having enhanced disease tolerance.

Indeed, the identification and production of disease tolerant plants will serve to improve the quantity, quality and longevity of food, such as fruits and vegetables, and other plant products such as flowers, thereby providing more products for market in both developed and underdeveloped countries. Moreover, the noninvasive technique of the present invention involving screening for ethylene insensitivity provides an easy, efficient and harmless procedure for identifying disease tolerant plants. The plant is neither injured nor destroyed by the process and remains edible and/or otherwise useful.

SUMMARY OF THE INVENTION

The present invention is directed to a process of identifying a plant having disease tolerance comprising administering to a plant an inhibitory amount of ethylene, and screening for ethylene insensitivity, thereby identifying a disease tolerant plant. Screening for ethylene insensitive plants includes screening for root or stem elongation and screening for an increase in ethylene production, both phenotypic characteristics of ethylene insensitive plants.

These and other aspects of the invention will become more apparent from the following detailed description when taken in conjunction with the following figures.

BRIEF DESCRIPTION OF THE FIGURES

FIG. 5 depicts a seedling body and developing plant. Specifically.

DETAILED DESCRIPTION OF THE INVENTION

Figure 1:
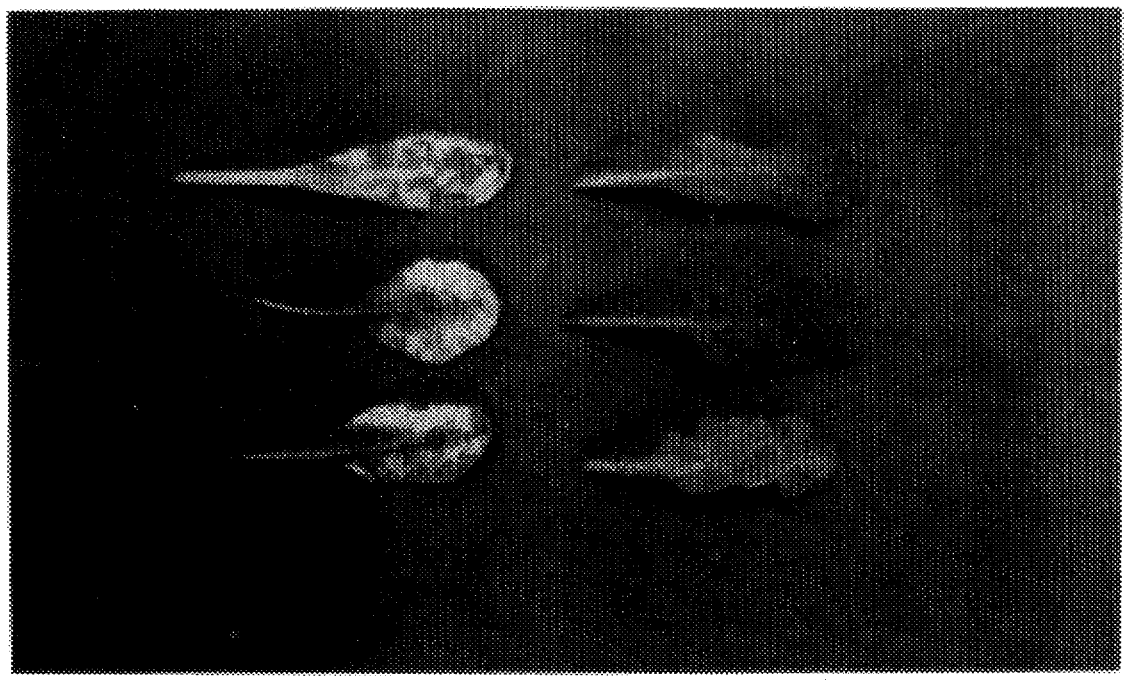
FIG. 1 shows leaves of Arabidopsis Col-0 (wild-type) and ein2-1 plants four days after inoculation with the virulent *Pseudomonas syringae* pv. *tomato* strain DC3000 (pLH12Ω). Plasmid pLH12Ω carries an insertionally inactivated, non-functional allele of avrRpt2. Leaves of intact plants were inoculated by vacuum infiltration of a $1 \times 10^5$ cfu/ml suspension of bacteria in 10 mM $MgCl_2$. Three representative leaves from each genotype were removed immediately prior to photography. Left column: Col-0; right column ein2-1.

The present invention is directed to a process for identifying a plant having disease tolerance by administering an inhibitory amount of ethylene to a plant and screening for ethylene insensitivity thereby identifying a disease tolerant plant. Screening includes screening for root or stem elongation, as well as screening for increased ethylene production, both phenotypic characteristics of ethylene insensitive plants.

In accordance with the present invention, disease tolerant plants which may be identified by the processes of the claimed invention include higher and lower plants in the Plant Kingdom. Mature plants and seedlings are included in the scope of the invention. A mature plant includes a plant at any stage in development beyond the seedling. A seedling is a very young, immature plant in the early stages of development.

Particularly preferred plants are those from: the Family Umbelliferae, particularly of the genera Daucus (particularly the species carota, carrot) and Apium (particularly the species *graveolens dulce*, celery) and the like; the Family Solanacea, particularly of the genus Lycopersicon, particularly the species *esculentum* (tomato) and the genus Solanum, particularly the species *tuberosum* (potato) and *melongena* (eggplant), and the like, and the genus Capsicum, particularly the species *annum* (pepper) and the like; and the Family Leguminosae, particularly the genus Glycine, particularly the species *max* (soybean) and the like; and the Family Cruciferae, particularly of the genus Brassica, particularly the species *campestris* (turnip), *oleracea* cv Tastie (cabbage), *oleracea* cv Snowball Y (cauliflower) and *oleracea* cv Emperor (broccoli) and the like; the Family Compositae, particularly the genus Lactuca, and the species *sativa* (lettuce), and the genus Arabidopsis, particularly the species *thaliana* (Thale cress) and the like. Of these Families, the most preferred are the leafy vegetables, for example, the Family Cruciferae, especially the genus Arabidopsis, most especially the species *thaliana*.

For purposes of the current invention, disease tolerance is the ability of a plant to survive infection with minimal injury or reduction in the harvested yield of saleable material. Plants with disease tolerance may have extensive levels of infection but have little necrosis and few to no lesions. These plants may also have reduced necrotic and water soaking responses and chlorophyll loss may be virtually absent. In contrast, resistant plants generally limit the growth of pathogens and contain the infection to a localized area with multiple apparent injurious lesions.

The current invention is directed to, for example, identifying plant tolerance to bacterial infections including, but not limited to *Clavibacter michiganense* (formerly *Coynebacterium michiganense*), *Pseudomonas solanacearum* and *Erwinia stewartii*, and more particularly, *Xanthomonas campestris* (specifically pathovars campestris and vesicatoria), *Pseudomonas syringae* (specifically pathovars tomato, maculicola).

In addition to bacterial infections, disease tolerance to infection by other plant pathogens is within the scope of the invention. Examples of viral and fungal pathogens include, but are not limited to tobacco mosaic virus, cauliflower mosaic virus, turnip crinkle virus, turnip yellow mosaic virus; fungi including *Phytophthora infestans, Peronospora parasitica, Rhizoctonia solani, Botrytis cinerea, Phoma lingam (Leptosphaeria maculans)*, and *Albugo candida*.

Figure 4:
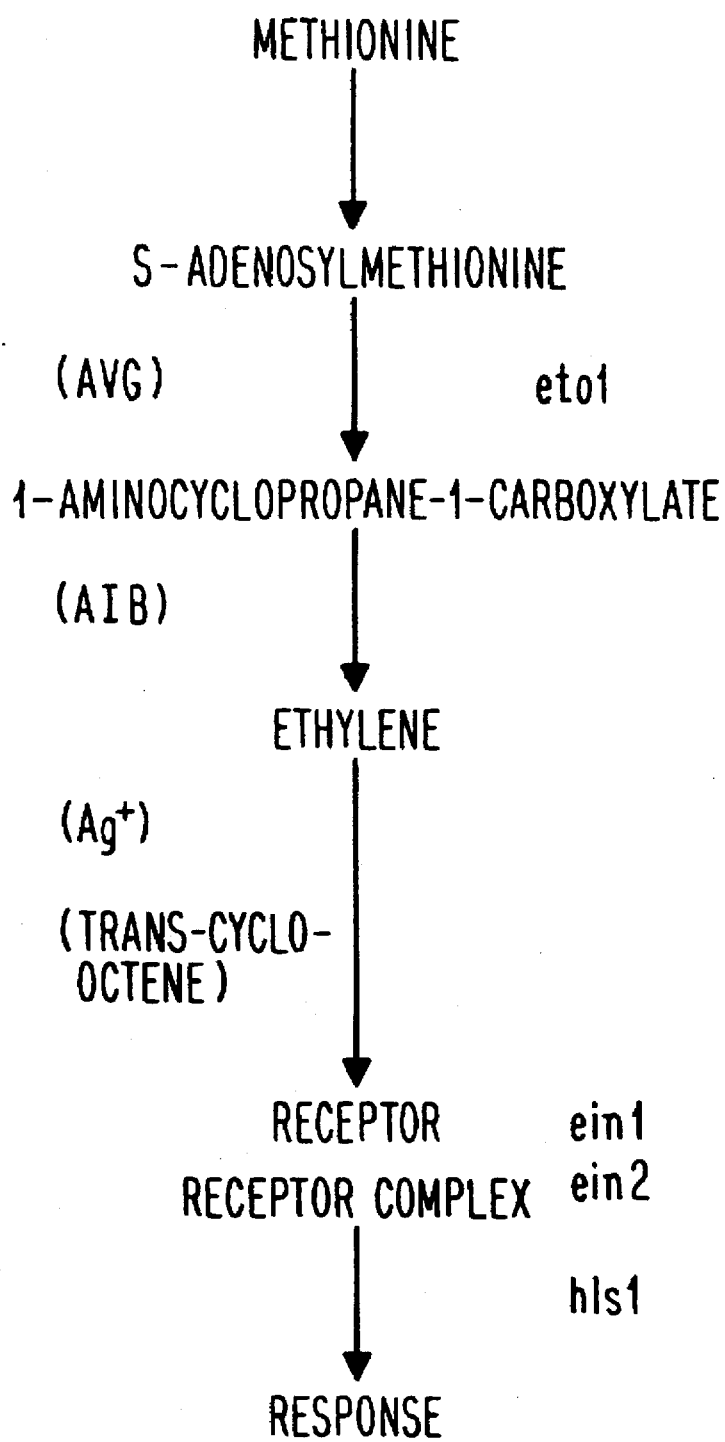
FIG. 4 is a schematic illustration of the ethylene biosynthesis pathway.

Ethylene, $CH_2=CH_2$, is a naturally occurring plant hormone. FIG. 4 depicts the ethylene biosynthesis pathway. The ethylene regulatory pathway includes the ethylene biosynthesis pathway and the ethylene autoregulatory or feedback pathway. In the ethylene biosynthesis pathway, methionine is converted to ethylene with S-adenosylmethionine (SAM) and 1-aminocyclopropane-1-carboxylic acid (ACC) as intermediates. These two reactions are catalyzed by ACC synthase and ethylene-forming enzyme (EFE), respectively. Little is known about the enzymes catalyzing these reactions and their regulation at the molecular level.

The receptor and receptor complex of FIG. 4 are believed to function with the autoregulatory pathway in the control of ethylene production. Ethylene regulatory pathway inhibitors are positioned along the left side of FIG. 4. The inhibitors include AVG (aminoethoxyvinyl-glycine) and AIB (α-aminoisobutyric acid). The steps at which the mutants, ethylene overproducer (etol), ethylene insensitive (ein1, ein2) and hookless (hls1), are defective appear on the right of FIG. 4.

In accordance with the claimed invention, ethylene insensitive plants are those which are unable to display a typical ethylene response when treated with high concentrations of ethylene. For purposes of the present invention, ethylene insensitivity includes total or partial inability to display a typical ethylene response. A typical ethylene response in wild type plants includes, for example, the so-called "triple response " which involves inhibition of root and stem elongation, radial swelling of the stem, and absence of normal geotropic response (diageotropism). Thus, for example, ethylene insensitive plants may be screened for in accordance with the present invention by the presence of an altered "triple response" wherein the root and stem are elongated despite the presence of high concentrations of ethylene. Further, a typical ethylene response also includes a shut down or diminution of endogenous ethylene production, upon application of high concentrations of ethylene. Ethylene insensitive plants may thus also be screened for, in accordance with the present invention, by the ability to continue production of ethylene, despite administration of high concentrations of ethylene. Such ethylene insensitive plants are believed to have impaired receptor function such that ethylene is constitutively produced despite the presence of an abundance of exogenous ethylene.

The present invention thus involves a process for identifying a plant having disease tolerance, comprising administering to a plant an inhibitory amount of ethylene and screening for ethylene insensitivity. Screening includes screening for root or stem elongation and screening for increased ethylene production. For purposes of the current invention, administration may be by any method for providing ethylene to a plant known to those of ordinary skill in the art, such as, but not limited to, growing plants in the presence of gaseous ethylene. An inhibitory amount of ethylene is any amount greater than that which would be produced endogenously by a normal, wild type plant under similar conditions. Suitable inhibitory amounts of ethylene for administration may include, for example, from about 100 to about 1 µl/L, more preferably from about 10 to about 1 µl/L, and even more preferably about 10 µl/L and about 5 µl/L. In addition, 1000 µl/L will identify highly ethylene insensitive plants.

Figure 5A:
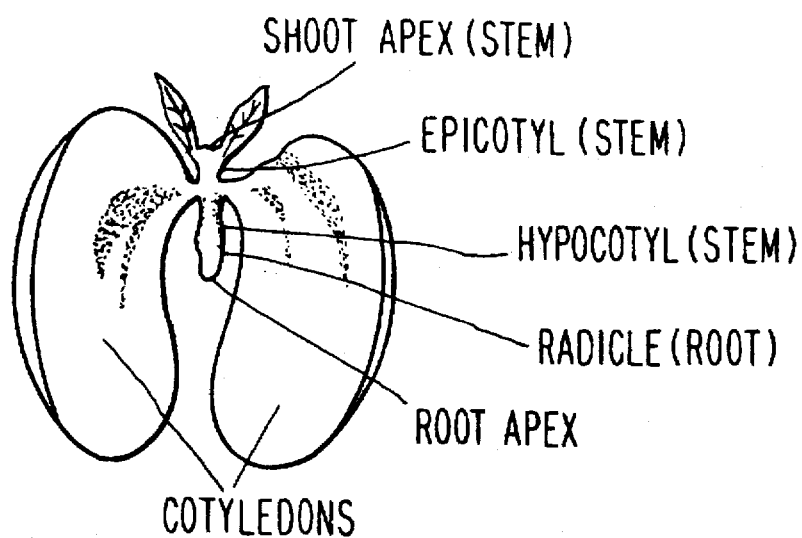
FIG. 5A is a cross section of the seedling body of a seed plant.
Figure 5B:
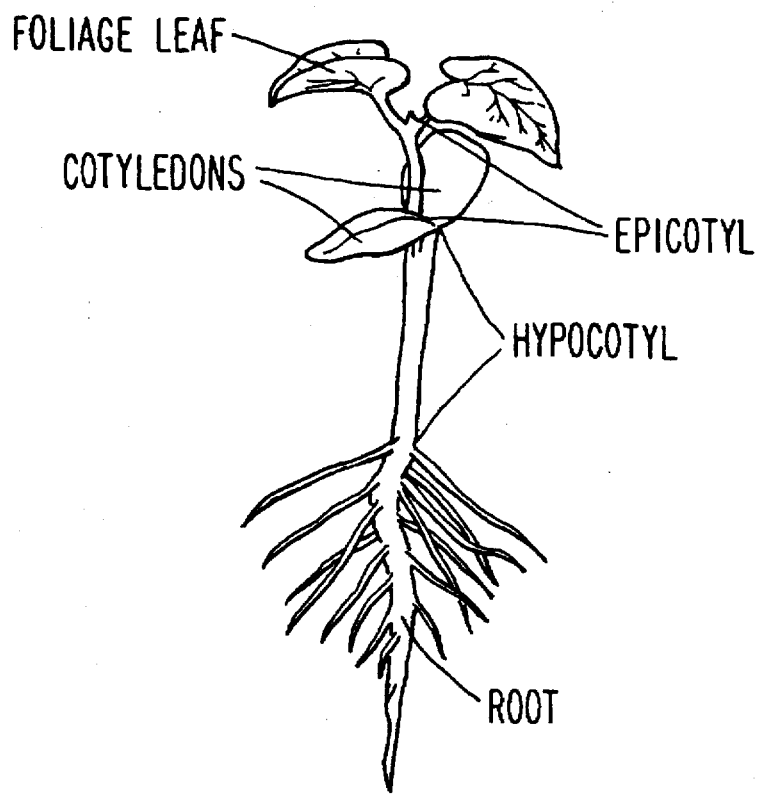
FIG. 5B is a perspective view of a developing seed plant.

As noted above, ethylene sensitive wild type plants experience an inhibition of root and stem elongation when an inhibitory amount of ethylene is administered. By inhibition of root and stem elongation, it is meant that the roots and stems grow less than the normal state (that is, growth without application of an inhibitory amount of ethylene). Typically, normal Arabidopsis (Col) grown without ethylene or ethylene precursor aminocyclopropane, ACC, root elongation is about 6.5±0.2 mm/3 days; normal stem elongation is 8.7±0.3 mm/3 days. Ein 2-1 plants grown without ethylene or ACC have root elongation of about 7.5±0.2 mm/3 days and stem elongation of 11.35±0.3 mm/3 days. In the presence of 100 µm ACC, Col root growth is 1.5±0.04 mm/3 days; ein 2-1 is 4.11±8.1 mm/3 days and stem growth of 3.2±0.1 mm/3 days for Col and 8.0±0.2 mm/3 days for ein 2-1. Alternatively, plants may be sprayed with ethaphon or ethrel. By roots, as used here, it is meant mature roots (that is, roots of any plant beyond the rudimentary root of the seedling), as well as roots and root radicles of seedlings. Stems include hypocotyls of immature plants of seedlings and stems, and plant axes of mature plants (that is, any stem beyond the hypocotyl of seedlings). See FIG. 5A and FIG. 5B.

Also as noted above, ethylene sensitive wild type plants experience a shut down or diminution of endogenous ethylene production, upon application of high concentrations of ethylene. In the ethylene insensitive plants identified by the processes of invention, the plants continue endogenous production of ethylene, despite administration of inhibitory amounts of ethylene. Ethylene production for wild type and ethylene insensitive mutants are shown in Table 1. An ethylene insensitive plant will produce an amount or have a rate of ethylene production greater than that of a wild type plant upon administration of an inhibitory amount of ethylene. As one skilled in the art will recognize, absolute levels of ethylene produced will change with growth conditions.

Disease tolerant plants identified in accordance with the process of the invention include, for example, plants containing the ein2 mutant genes. The ein1 and ein2 mutant genes are well known in the art, although until the present invention, plants containing such genes were not identified as possessing disease tolerance. Ein1 and ein2 mutants are described for example in, Guzman et al., "Exploiting the Triple Response of Arabidopsis to Identify Ethylene-Related Mutants", *The Plant Cell*, Vol. 2, pp. 513–523 (1990), the disclosures of which are hereby incorporated herein by reference, in their entirety.

The present invention is further described in the following examples. These examples are not to be construed as limiting the scope of the appended claims.

EXAMPLE 1

Production of Arabidopsis mutants

The production of plants which exhibit enhanced disease tolerance were investigated with the use of Arabidopsis mutants ein, which are insensitive to ethylene and are derived from Arabidopsis Col-0. The ein mutants were prepared according to the method of Guzman et al., *The Plant Cell*, Vol. 2, pp. 513–523 (1990), the disclosures of which are hereby incorporated herein by reference, in their entirety.

*Arabidopsis thaliana* Strains and Growth Conditions

*Arabidopsis thaliana* ecotype Columbia was the parental strain for the isolation of triple response mutants. Ecotypes Landsberg and Niederzenz were used for mapping purposes. (Seeds were obtained from Dr. Nigel Crawford, University of California, San Diego.) Etiolated Arabidopsis seedlings were grown as follows: seeds were surface sterilized for 8 min in 5% sodium hypochlorite (Clorox) and plated in Petri plates containing growth medium consisting of Murashige and Skoog salts (MS, GIBCO) (pH 5.7) supplemented with 10 g/L sucrose, 1 mg/L thiamine HCl, 0.5 mg/L pyridoxine,, 0.5 mg/L nicotinic acid, 100 mg/L inositol, and 0.8% agar (bacto-agar, Difco). Seeds were planted with top agarose consisting of 0.6% low-melting point agarose in MS salts. After cold treatment at 4° C. for 4 days, the plates were incubated in the dark for 23° C. for 66 hr to 72 hr. Plants were grown to maturity in a growth chamber at 22° C. to 25° C. under continuous illumination with fluorescent and incandescent light. Seeds were planted in Metro-Mix 200 (Grace), and modified Hoagland's nutrient media (Feldmann and Marks, 1987) was subirrigated every 3 days.

Induction and Isolation of Mutants

Stocks of mutagenized seeds were obtained by chemical mutagenesis with ethyl methanesulfonate (EMS). *A. thaliana* (Columbia) seeds were hydrated in distilled water overnight at 4° C. and then treated with 0.4% EMS (Sigma) buffered in 100 mM sodium phosphate (ph 7.0) for 8 hr. Lots of 1500 to 2000 M1 seeds were planted separately to obtain independent populations of mutagenized M2 generation seeds. Approximately 15,000 to 20,000 M2 seeds were screened per lot. M2 seeds were surface sterilized and plated with low-melting-point agarose in Petri plates containing growth media. After 4 days of incubation at 4° C., seeds were placed at 23° C. in the dark for 66 hr to 72 hr. To avoid the possible effects of ethylene accumulation in Eto and Hls screens, M2 seeds were planted at low density, about 1000 seeds per Petri plate (150×15 mm). The Ein screen was performed by incubating seeds in the dark in a flow-through chamber where 10 μL/L ethylene (Airco) was continuously delivered; M2 seeds were planted at a density of 10,000 per Petri plate (150×15 mm).

After selection, the putative mutants were transferred to the soil and allowed to self-pollinate, and the progeny (M3 seeds) were retested for the mutant phenotype. For Eto, 64 seedlings were identified from eight lots of M2 seeds; out of 26 plants that survived, two showed the phenotype. For Hls, 27 seedlings were isolated from six lots of M2 seed; of eight plants that survived, two showed the mutant phenotype. For Ein, 25 seedlings that showed the mutant phenotype survived and six were further analyzed.

Genetic Analysis

Crosses were performed as follows: two or three unopened flowers from the main inflorescence were emasculated with the help of a pair of fine forceps under a dissecting microscope, and several anthers from the male donor were used to pollinate the recipient stigmas. The rest of the flowers from the inflorescence were removed. To obtain the chromosomal location of the ein mutations, W100 (ecotype Landsberg) (Koornneef et al., 1987) was used as a mapping strain. W100 has two visible markers on each of the five chromosomes; our W100 stock does not carry the ms-1 (male sterile) marker. Pollen from the W100 tester strain was crossed to ein1-1 and ein2-1 plants. The Ein F2 plants were chosen and segregation of visible markers was determined. An average population of 49 plants was examined for each cross.

To obtain the progeny for RFLP analysis, ein2 mutants (ecotype Columbia) were crossed to wild-type plants of the ecotype Niederzenz. The F1 plants were allowed to self-fertilize, and DNA from single F2 plants homozygous recessive for the ein2 mutation was prepared. An average population of 64 plants was considered for each analysis. Recombination frequencies were calculated using the RECF2 program developed by M. Koornneef (Agricultural University, Wageningen). Procedures for plant DNA isolation (Deblaere et al., 1987), probe preparation (Blattner et al., 1978, Feinberg and Vogelstein, 1983), and blot hybridization (Maniatis et al. 1989) have been described.

Determination of Ethylene Accumulation

Before physiological examination the mutants were backcrossed to the wild type at least once. More than 95% germination was obtained from wild-type etol, hls1, ein1, and ein2 strains when they were cold-treated for 4 days before germination. Surface-sterilized seeds (approximately 500) were germinated and grown for 66 hr to 72 hr in the dark at 23° C. in 20 mL gas chromatograph vials containing 15 mL of growth medium. To measure the conversion of exogenous ACC to ethylene, seedlings were grown in 1% low-melting-point agarose buffered with 3 mM Mes at pH 5.8. In this solid support no chemical formation of ethylene from ACC was detected at any of the concentrations of ACC employed. Ethylene accumulation from tissues of mature plants (100 mg) was measured after overnight incubation in 20 mL gas chromatograph vials. Leaves and inflorescence were taken from 24 day old to 28 day old plants, siliques from 32 day old to 36 day old plants. Each value represents the mean obtained from three to six samples. Accumulation of ethylene was determined by gas chromatography using a photo-ionization detector (HNU) and a Hewlett Packard HP5890A gas chromatograph equipped with an automated headspace sampler. A certified standard of 10 μL/L ethylene (Airco) was used to calculate ethylene concentrations. The concentration of the inhibitors of ethylene biosynthesis and ethylene action was determined empirically. AVG, α-aminoisobutyric acid, and $AgNo_3$ were supplemented to the media at 5 μM, 2 mM, and 0.1 mM, respectively, trans-Cyclooctene (17 μL/L) was injected to the vial after the cold treatment. Specifically, twenty five independent ethylene-insensitive mutants were isolated; six mutants which showed at least three-fold difference in the length of the hypocotyl compared with ethylene-treated wild-type hypocotyl, were further characterized. In these mutants, the apical hook was either present, absent or showed some curvature in the apical region. The appearance of the apical curvature was dependent on the duration of the incubation. After more than 3 days of incubation in the dark with 10 μL/L ethylene, the apical curvature was absent. This phenotype was named ein for ethylene insensitive.

Mendelian analysis indicated that insensitivity to ethylene was inherited as either a dominant or recessive trait depending on the mutation studied. Complementation analysis was performed with five recessive mutants to determine whether more than one locus was involved in this phenotype. The results of these studies indicated that all five recessive mutations were allelic. The ein phenotype was tested for linkage to nine visible markers to determine whether the recessive and dominant ein mutations were allelic. The dominant ein mutation was mapped close to the mutation ap-1 locus on chromosome 1 and was named ein1-1. None of the nine markers showed linkage to the recessive ein mutation. Restriction fragment length polymorphism (RFLP) analysis was performed to map this mutation. Randomly selected RFLP probes were initially used to assess linkage. After testing probes from three different chromosomes, linkage was detected to one RFLP from chromosome 4 and named ein2-1. This observation was confirmed using additional RFLP probes from the same chromosome. Further experimentation confirmed ein2-2, ein2-3, ein2-4 and ein2-5 to be alleles of ein2-1.

Growth features of ethylene insensitive mutants were also observed. After seedlings were planted in soil and cold treated at 4° C. for 4 days, the seedlings were incubated in the dark at 23° C. for 66-72 hours. Plants were grown to maturity in a growth chamber at 22° C. to 25° C. under continuous illumination with fluorescent and incandescent light. The rosette of ein1-1 and ein2-1 plants was larger compared with the wild type, Col-0, rosette and a delay in bolting (1 cm to 2 cm growth in the length of the stem) was observed. These observations indicated that the ethylene insensitive mutations identified at the seedling stage exerted remarkable effects during adult stages of growth.

Eto mutants, which constitutively produce ethylene, were initially screened by observing a constitutive triple response; seedlings with inhibition of hypocotyl and root elongation, swelling of the hypocotyl and exaggerated tightening of the apical hook. Mendelian segregation analysis determined the genetic basis of these mutations to be a single recessive mutation and identified as an ethylene overproducer or eto.

Etol, ein1 and ein2 mutants were analyzed to determine ethylene accumulation. The mutants were backcrossed to the wild type before physiological examination. Surface-sterilized seeds (about 500) were germinated and grown for 66 to 72 hours in the dark at 23° C. in 20 ml gas chromatograph vials containing 15 ml of growth medium.

To measure the conversion of exogenous 1-aminocyclopropane-1-carboxylic acid (ACC, an intermediate in ethylene production) to ethylene, seedlings were grown in 1% low-melting-point agarose buffered with 3 mM Mes at pH 5.8. In this solid support no chemical formation of ethylene from ACC was detected at any of the concentrations of ACC employed.

Ethylene accumulation from tissues of mature plants (100 mg) was measured after overnight incubation in 20 ml gas chromatograph vials. Leaves and inflorescence were taken from 24–28 day old plants, siliques from 32–36 day old plants. Accumulation of ethylene was determined by gas chromatography using a photo-ionization detector (HNU) and a Hewlett Packard HP5890A gas chromatograph equipped with an automated headspace sampler. A certified standard of 10 μl/L ethylene (Airco) was used to calculate ethylene concentrations. The concentration of the inhibitors of ethylene biosynthesis and ethylene action was determined empirically. For eto mutants, AVG, α-aminoisobutyric acid, and AgNO$_3$ supplemented the media at 5 μM, 2 mM and 0.1 mM, respectively and trans-cyclooctene (17 μl/L) was injected into the vial after the cold treatment. Ethylene production was increased significantly in the dominant ein1-1 mutant and the recessive ein2-1 mutant, see Table 1. Ethylene production was inhibited in eto1-1 seedlings that were grown in media supplemented with ethylene inhibitors aminoethoxyvinylglycine, AGV and α-aminoisobutyric acid, AIB, see Table 1.

TABLE 1

Ethylene Production in Triple Response Mutants

| Strain | Ethylene Accumulation |
|---|---|
| Wild type | |
| Etiolated seedling | 6.76 ± 0.68 nl/g |
| Leaves | 73.01 ± 17.64 nl/g |
| eto1-1 | |
| Etiolated seedling | 276.72 ± 53.70 nl/g |
| Leaves | 174.39 ± 29.18 nl/g |
| ein1-1 | |
| Etiolated seedling | 12.73 ± 2.79 nl/g |
| Leaves | 222.95 ± 70.29 nl/g |
| ein2-1 | |
| Etiolated seedling | 20.69 ± 2.09 nl/g |
| Leaves | 136.59 ± 26.89 nl/g |

Another ethylene insensitive mutant of *Arabidopsis thaliana* was designated etr by Bleecker et al. in "Insensitivity to Ethylene Conferred by a Dominant Mutation in *Arabidopsis thaliana*", *Science*, Vol. 241, pp. 1086–1089 (1990), the disclosures of which are hereby incorporated herein by reference, in their entirety. Etr was identified by the ethylene-mediated inhibition of hypocotyl elongation in dark-grown seedlings. Populations of M$_2$ generation from mutagenized seed of *Arabidopsis thaliana* were plated on a minimal medium solidified with 1% agar and placed in a chamber through which 5 μl/L ethylene in air was circulated. Seedlings that had grown more than 1 cm after 4 days were selected as potential ethylene insensitive mutants. A screen of 75,000 seedlings yielded three mutant lines that showed heritable insensitivity to ethylene. Hypocotyl elongation of etr mutant line was unaffected by ethylene at concentrations of up to 100 μl/L, while elongation of the wild type was inhibited by 70% with ethylene at 1 μl/L.

EXAMPLE 2

Preparation of Bacterial Strains, Plasmids and Recombinant DNA for Inoculation and Disease Scoring

*Pseudomonas syringae* pv. *tomato*, Pst, strain DC3000 derivatives were used to inoculate Arabidopsis leaves. Avirulence gene avrRpt2 was cloned into plasmids pABL18 or pLH12, avirulence gene avrB was cloned into plasmid pPSG0002, and avirulence gene avrRpm1 was cloned into plasmid K48 to produce avirulent strains. DC3000 carrying no plasmid, pLAFR3 (vector with no insert), or pLH12Ω (insertionally inactivated avrRpt2 on plasmid pLAFR3) are designated "Virulent Pst".

For the production of virulent strains, DC3000 and *Pseudomonas syringae*, pv. *maculicola* strain 4326 were cultured at 28° C. on King's medium B. King, E. O. et al. "Two simple Media for the Demonstration of Pyrocyamin and Fluorescein" *J. Lab. Clin. Med.*, Vol. 44, pp. 301–307 (1954)). Bacto agar at 1.5% (w/v) was added to the media for plate cultures. Antibiotics were used for selection at the following concentrations: tetracycline, 10–20 mg/L; rifampicin, 100 mg/L; spectinomycin, 20 mg/L; streptomycin, 30 mg/L; cyclohexamide, 50 mg/L. The broad host range vector pLAFR3 were used for the cosmid library and for subclones. The omega (Ω) fragment encoding Sp$^r$ was used for site-directed mutagenesis.

*Xanthomonas campestris* pv. *campestris*, Xcc, strain 2669, grown on NYGA medium, was also used to inoculate Arabidopsis. Daniels, M. J. et al. "Isolation of Mutants of *Xanthomonas campestris* pv. *campestris* Showing Altered Pathogenicity", *J. Gen. Microbiol.*, Vol. 130, pp. 2447–2455 (1984).

*Pseudomonas syringae* pv. *maculicola*, Psm, strain 4326 was also used.

Standard techniques for DNA subcloning, plasmid preparations and agarose gel electrophoresis of DNA fragments were used as in Ausubel et al., *Current Protocols In Molecular Biology*, Wiley-Interscience, New York (1987) and Sambrook et al., *Molecular Cloning: A Laboratory Manual*, 2nd ed., Cold Spring Harbor Laboratory Press, Cold Spring Harbor, N.Y. (1989).

More specifically, in the production of pABL18 or pLH12 with avrRpt2, genomic cosmid libraries of Pst were prepared in the vector pLAFR3 as described by Swanson et al., "Cloned Avirulence Gene of *Xanthomonas campestris* pv. *vesicatoria* Complements Spontaneous Race Change Mutant", *Mol. Plant-Microbe Interact.*, Vol. 1, pp. 5–9 (1988). Genomic DNA from *Pseudomonas syringae* pv. *tomato* strain 1065 was purified, partially digested with restriction endonuclease Sau3A, ligated into pLAFR3, packaged in cosmid packing extract, and transfected into *E. coli*. Individual colonies of *E. coli* (containing a clone of a single pLAFR3-based library constituent) were isolated and used in triparental matings to move the pLAFR3-based DNA construct into *Pseudomonas syringae* pv. *tomato* strain DC3000. Many hundred DC3000 clones (each carrying a single region of the 1065 genome on cosmid vector pLAFR3) were screened for acquired avirulence by inoculation into *Arabidopsis thaliana* Col-0 leaves. DC3000 carrying cosmid p4-24 did not cause extensive lesions and cosmid p4-24 was therefore studied further. Avirulence locus avrRpt2 was subcloned from cosmid p4-24 by partial digestion with Sau3A, 3–5 kb fragments were gel purified and ligated into the BamHI site of pLAFR3. Active constructs pABL18 and pLH30 containing 3.6 kb and 3.7 kb inserts, respectively, were identified by conjugation into Pst strain DC3000 and testing on *Arabidopsis ecotype* Col-0.

The inserts in these two clones overlapped by 2.2 kb. A 1.4 kb HindIII fragment that was contained within this overlap was then isolated from pLH30 and cloned into pLAFR3 to yield pLH12. pLH12 avirulence activity was disrupted by insertion of an Ω fragment (Sp'/Sm'). Prentki and Krisch, "In Vitro Insertional Mutagenesis with a Selectable DNA Fragment", Gene, Vol. 29, pp. 303–313 (1984) into the SacI site located 0.7 kb from either end of the insert.

The plasmids pPSG0002 (carrying avrB) and K48 (carrying avrRpm1) were produced by the process described above for pABL18 and pLH12 (carrying avrRpt2). The specific materials used in the production of pPSG0002 and K48 (genomic DNA, restriction endonucleases, bacterial strains, and plant genotypes) are published in Staskawicz et al., "Molecular Characterization of Cloned Avirulence Genes from Race 0 and Race 1 of *Pseudomonas syringae* pv. *glycinea*", *J. Bacteriol.*, Vol. 169, p. 5789 (1987), and in Debener et al., "Identification and Molecular Mapping of a Single *Arabidopsis thaliana* Locus Determining Resistance to a phytopathogenic *Pseudomonas syringae* Isolate", *The Plant Journal*, Vol. 1, pp. 289–302 (1991).

EXAMPLE 3

Plant Inoculation and Disease Scoring

To assay for a hypersensitive response, avirulent *Pseudomonas syringae* pv. *tomato* strains were resuspended at $OD_{600}$ of 0.02, applied by pipet infiltration, and leaves were scored for tissue collapse one day after inoculation.

Resistant Arabidopsis infected with avirulent bacteria induce a hypersensitive response (HR) within 24 hours. Pipet inoculation of leaves with a high concentration of bacteria ($>2\times10^7$ cfu/ml) provides a convenient assay for active resistance, since the HR is readily detectable as a large region of collapsed tissue. No collapse is observed in the first 24 hours following inoculations involving plants that lack resistance or pathogens that lack avirulence. Wild-type Col-0 plants and those carrying ein1-1, ein2-1, and eto1-1 mutations were inoculated by this method using isogenic Pst DC3000(pABL18) and DC3000(pLAFR3). All plant genotypes tested elaborated a strong HR following inoculation with Pst carrying avrRpt2, and gave no HR in response to virulent controls. Hypersensitive response was measured by a showing of localized cell death and physical isolation of pathogen, see Table 2. Leaves were scored five days after inoculation unless otherwise noted. For each leaf, severity of visible disease symptoms was rated on a one to five scale, 1=no symptoms, 5=confluent necrosis as seen in Table 2. Numbers are the mean ± one standard error of the mean. Ratings followed by the letter d are significantly different from the score for Col-0 infected with the same bacterial strain (p less than 0.05, Wilcoxon two-sample test).

Additional pathogen avirulence genes were sought to test whether the above results could be generalized beyond resistance to pathogens carrying avrRpt2. Previously cloned avirulence genes were tested for function during infection of Arabidopsis. The avrB locus from *P. syringae* pv. *glycinea* was observed to convert virulent Pst strains to avirulence on Arabidopsis ecotype Col-0. In addition, avrRpm1 from *P. syringae* pv. *maculicola* was found to cause avirulence in infections of Arabidopsis Col-0. When wild-type, ein1-1, ein2-1, and eto1-1 lines were inoculated with Pst carrying avrB or avrRpm1, resistance was observed in all cases. Disease development was minimal in inoculations at low bacterial concentration (Table 2). For each leaf, severity of visible disease symptoms was rated on a one to five scale, 1=no symptoms, 5=confluent necrosis as seen in Table 2. Numbers are the mean ± one standard error of the mean. Ratings followed by the letter d are significantly different from the score for Col-0 infected with the same bacterial strain (p less than 0.05, Wilcoxon two-sample test).

Furthermore, a macroscopically evident hypersensitive response was observed on wild-type, ein1-1, ein2-1, and eto1-1 plants following pipet inoculation at $2\times10^7$ cfu/ml with Pst carrying avrB or avrRpm1.

Disease lesions closely resembling those formed in moderate to severe natural infestations involving Pst were also produced by dipping leaves in a bacterial suspension containing the surfactant L-77, or by vacuum infiltration. For surfactant inoculation, freshly grown bacteria were resuspended in 10 mM $MgCl_2$ at an $OD_{600}$ of between 0.2 and 0.3, and Silwet L-77 (Union Carbide) was added to a final concentration of 0.02%. L-77 is a silicon-based copolymer that depresses surface tension sufficiently to allow aqueous droplets to spread evenly over the leaf surface and to penetrate stomatal openings. Entire rosettes (grown under light of >150 $\mu mol\cdot s^{-1}\cdot m^{-2}$) were dipped briefly in this solution, maintained at high relative humidity for one day and then in normal growth chamber conditions, and lesions were scored on the fourth day after inoculation.

For vacuum infiltration, freshly grown bacteria were resuspended and diluted in 10 mM $MgCl_2$ to approximately $1\times10^5$ cfu/ml. Entire rosettes were infiltrated and plants were returned to growth chambers. Using these methods, mutant ein1-1, ein2-1, and eto1-1 plants were inoculated with Pst carrying avrRpt2. All plant genotypes tested resembled wild-type in displaying only occasional and minor disease symptoms following inoculation with this avirulent strain.

It was previously shown that the leaves of resistant plants inoculated with avirulent Pst strains at lower bacterial concentrations develop few or no symptoms, while susceptible hosts or hosts infected with virulent Pst strains display necrotic lesions with chlorotic margins three to five days after infection.

When plants were inoculated by pipet infiltration with $1\times10^6$ cfu/ml of Pst carrying avrRpt2, the leaves of ein1-1, ein2-1, and eto1-1 mutants resembled the wild-type Col-0 line and developed only minimal disease symptoms, see Table 2. Similar results were obtained with Arabidopsis lines carrying different alleles of the ethylene-insensitivity loci, etr1, ein2-3, ein2-4, and ein2-5.

TABLE 2

Disease Phenotypes of Arabidopsis Plants Inoculated with Avirulent Bacterial Pathogens

| Avirulent Bacterial Strain | Arabidopsis line | | | |
|---|---|---|---|---|
| | Col-0 | ein1-1 | ein2-1 | eto1-1 |
| Pst + avrRpt2 | 1.8 ± 0.2 | 2.3 ± 0.2 | 1.2 ± 0.1d | 2.5 ± 0.3 |
| Pst + avrB | 1.5 ± 0.3 | 1.7 ± 0.3 | 1.0 ± 0.1 | 1.7 ± 0.4 |
| Pst + avrRpm1 | 1.3 ± 0.2 | 1.7 ± 0.3 | 1.0 ± 0 | 1.5 ± 0.2 |

For freshly grown virulent bacteria, strains were resuspended and diluted in 10 mM $MgCl_2$ to an $OD_{600}$ of 0.001 (approximately $1\times10^6$ colony forming units per milliliter (cfu/ml)) for *Pseudomonas syringae* pv. *tomato* and *maculicola* and to an $OD_{600}$ of 0.02 (approximately $2\times10^7$ cfu/ml) for *Xanthomonas campestris* pv. *campestris*. A plastic Pasteur pipet was used to introduce approximately 10 μl into the mesophyll of intact Arabidopsis leaves. Leaves were scored five days after inoculation unless otherwise noted. For each leaf, severity of visible disease symptoms was rated on a one to five scale, 1=no symptoms, 5=confluent necrosis as seen in Table 3. Numbers are the mean ± one standard error of the mean. Ratings followed by the letter d are significantly different from the score for Col-0 infected with the same bacterial strain (p less than 0.05, Wilcoxon two-sample test).

In contrast to the results with Pst strains carrying avrRpt2, avrB, or avrRpm1, the development of disease symptoms upon inoculation with virulent Pst strains was clearly different for one class of mutants. The leaves of Col-0, ein1-1, and eto1-1 mutants developed pale necrotic or water-soaked lesions surrounded by chlorotic tissue. However, ein2-1 plants showed almost no chlorosis and less frequent water-soaking. When plants were inoculated with virulent Pst by the L-77 surfactant or vacuum infiltration methods, disease symptoms were again observed on wild-type, ein1-1, and eto1-1 genotypes but were virtually absent from ein2-1 plants.

Disease lesions were not observed in control inoculations having no bacteria, for virulent and avirulent experiments. To monitor growth of bacteria in Arabidopsis leaves, two leaf disc samples (0.125 cm$^2$ each) were removed from each vacuum infiltrated plant at the designated times after infection, samples from two plants were pooled and homogenized in 10 mM MgCl$_2$, and the number of bacterial colony forming units per cm$^2$ of leaf area (cfu/cm$^2$) was determined by dilution plating on King's B agar containing rifampicin (100 mg/liter) and cyclohexamide (50 mg/liter). Bacteria were also enumerated using individual 0.125 cm discs taken from leaves inoculated by pipet infiltration. Leaf chlorophyll content was determined by the method of Lichtenthaler and Wellburn.

TABLE 3

Disease Phenotypes of Arabidopsis Plants Inoculated with Virulent Bacterial Pathogens

| Virulent Bacterial Strain | Arabidopsis line | | | |
|---|---|---|---|---|
| | Col-0 | ein1-1 | ein2-1 | eto1-1 |
| Pst | 4.0 ± 0.2 | 4.2 ± 0.2 | 1.9 ± 0.2d | 4.0 ± 0.3 |
| Psm | 4.3 ± 0.2 | 4.0 ± 0.4 | 2.2 ± 0.3d | 4.5 ± 0.2 |
| Xcc | 3.7 ± 0.4 | 3.3 ± 0.2 | 1.6 ± 0.2d | 3.5 ± 0.4 |

FIG. 1 shows leaves taken from vacuum infiltrated plants four days after inoculation. Col-0 leaves had developed both individual and coalesced necrotic lesions, and showed extensive chlorosis. Leaves on ein2-1 mutants were largely unaffected. By the seventh day after inoculation, many of the leaves on wild-type Col-0 plants had become completely chlorotic and dead, whereas the ein2-1 mutants showed only minimal symptoms. By any of the three inoculation methods, ein2 leaves that were relatively free of symptoms four or five days after inoculation remained similarly free of symptoms when observed two weeks after inoculation.

Plants were also inoculated with virulent strains of two other Arabidopsis pathogens, P. syringae pv. maculicola and X. campestris pv. campestris, to test whether the ein2 result was in some way unique to the Arabidopsis/Pst interaction. Following inoculation with Psm, the ein2 plants showed significantly less disease than wild-type, ein1-1 or eto1-1, see Table 3. Xcc was not as virulent as Pst or Psm in the conditions used, but inoculated ein2 plants once again developed far less necrosis or chlorosis than the other genotypes, see Table 3.

In a subset of the experiments summarized in Table 3, leaves were also scored three days after inoculation to assay for exceptionally early symptom appearance. The only statistically significant difference from wild-type Col-0 observed was for eto1-1 leaves inoculated with Xcc (day three disease scores: Col-0/Xcc, 1.8±0.3; eto1-1/Xcc, 3.4±0.3). Prematurely strong symptoms were also observed in some eto1-1 leaves inoculated with virulent Pst, but this difference was not reproducible (day three disease scores: Col-0/Pst 2.9±0.3; eto1-1/Pst 3.3±0.2).

Figure 2:
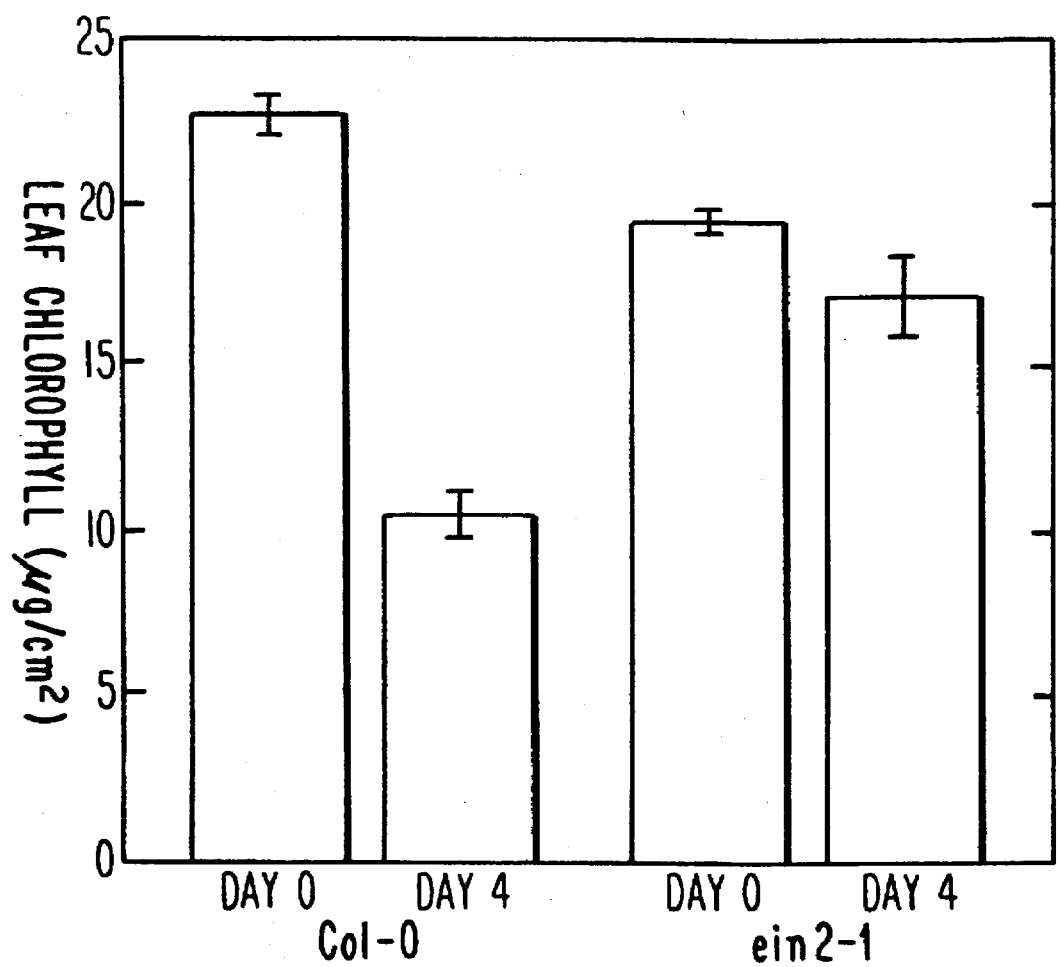
FIG. 2 depicts loss of chlorophyll in Arabidopsis Col-0 and ein2-1 leaves inoculated with the virulent *Pseudomonas syringae* pv. *tomato* strain DC3000. Plants were inoculated by vacuum infiltration of a $1 \times 10^5$ cfu/ml bacterial suspension. Leaf samples were taken one hour and four days after inoculation and assayed for chlorophyll content. Values presented are the mean ± one standard error of the mean.

Differences in the extent of leaf chlorosis between infected ein2-1 and wild-type Arabidopsis were quantified by chlorophyll assays. By the fourth day after inoculation with virulent Pst, total leaf chlorophyll (chlorophyll a+b) in wild-type Col-0 had dropped to 47% of the original level while total chlorophyll only fell to 89% of the original level in ein2-1 plants (FIG. 2). Changes in chlorophyll a and for chlorophyll b paralleled the pattern for the summed values presented in FIG. 2.

In order to confirm that decreased susceptibility to virulent Pst was caused by alterations at ein2 and not by other coincidentally present mutations, plants carrying independently derived ein2 alleles were examined. Leaves were inoculated by pipet infiltration with a 1×10$^6$ cfu/ml suspension of virulent Pst. While wild-type Col-0 plants developed extensive lesions, individuals homozygous for ein2-3, ein2-4, or ein2-5 resembled ein2-1 and showed few if any disease symptoms. Mean disease severity scores 1 one standard error of the mean for ein2-3, ein2-4, ein2-5 plants were 2.3±0.3, 2.2±0.4, and 2.0±0.2 respectively. Arabidopsis carrying etr1 (a stronger allele of the ein1 locus) were similar to ein1-1 plants, developing extensive disease symptoms following inoculation with virulent Pst by both pipet and vacuum infiltration methods.

Figure 3A:
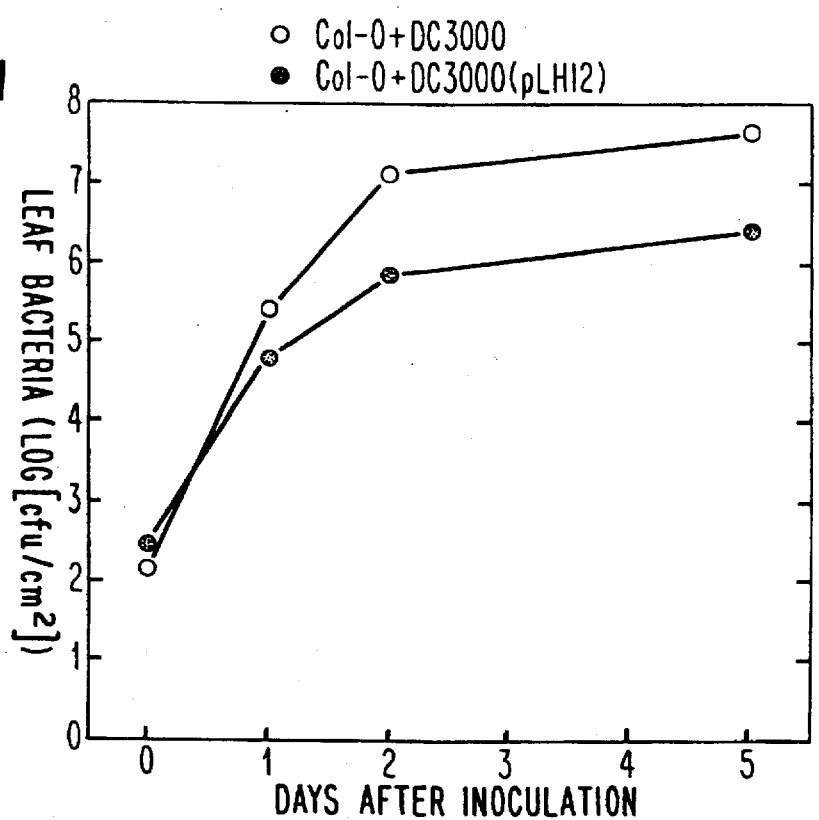
FIG. 3A and 3B exhibits growth of virulent (o) or avirulent (•) *Pseudomonas syringae* pv. *tomato* in Arabidopsis Col-0 (FIG. 3A) and in ein2-5 mutants (FIG. 3B). DC3000 (pLH12) carries avrRpt2 as a 1.4 kb fragment cloned into pLADR3; pLH12Ω carries an insertionally inactivated allele of avrRpt2. Leaves of intact plants were inoculated by vacuum infiltration of a $1 \times 10^5$ cfu/ml suspension of bacteria in 10 mM $MgCl_2$. Two leaf disc samples (0.125 $cm^2$ each) were removed from each plant at the designated times after infection, samples from two plants were pooled and homogenized in 10 mM $MgCl_2$, and the number of bacterial colony forming units per $cm^2$ of leaf area ($cfu/cm^2$) was determined by dilution plating on selective media. Values presented are the mean for six plants; standard error of the mean was less than 0.15 log ($cfu/cm^2$) for every data point.
Figure 3B:
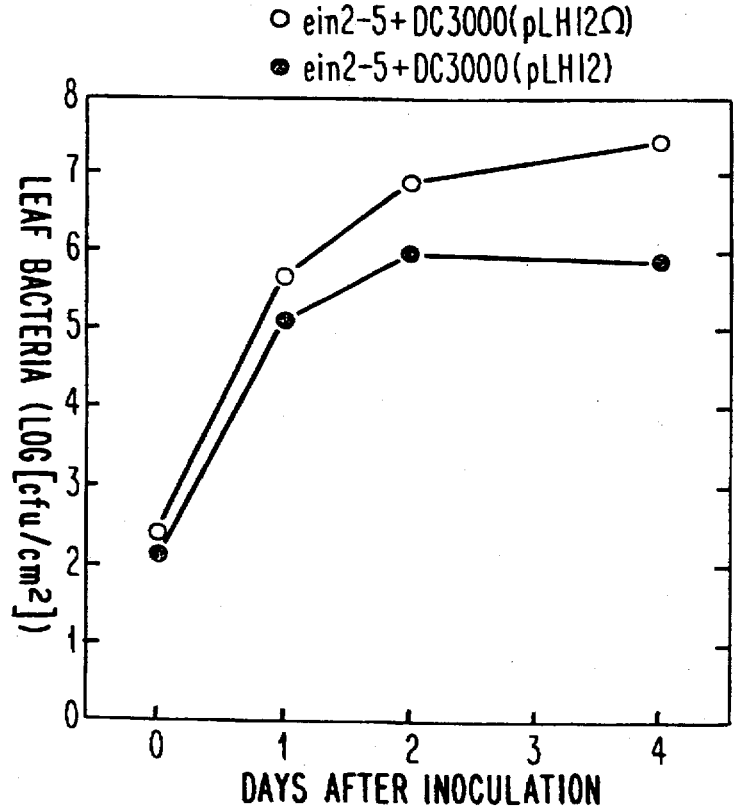

A common characteristic of plant resistance to bacterial infection is the relative restriction of pathogen multiplication within the plant. Virulent Pst strains have been shown to increase more than 10$^5$ fold in Arabidopsis Col-0 leaves while isogenic strains carrying the cloned avirulence gene avrRpt2 on RP4-derived plasmids grow to levels fifty fold lower. Bacterial population sizes in ein2 and wild-type Col-0 leaves were examined following inoculation by vacuum infiltration of a solution containing 1×10$^5$ cfu/ml bacteria (FIG. 3). As expected from visual scoring of infected leaves, growth of avirulent Pst was restricted by both wild-type and ein2-5 plants. Surprisingly, the isogenic Pst strain without avrRpt2 grew to similar levels in both wild-type and ein2 plant lines. Visible damage was minimal on ein2 plants infected with virulent Pst (discussed above and shown in FIG. 1) even though bacteria were present in large numbers. Similar results were obtained in vacuum infiltration experiments with ein2-1 plants, and also when leaf bacteria were enumerated following pipet infiltration; symptom development differed between ein2 and wild-type Arabidopsis despite the presence of similar numbers of the virulent Pst strain DC3000.

EXAMPLE 4

Inoculation of Plants with Coronatine

Coronatine, a phytotoxin produced by many Pseudomonas syringae strains, has structural similarity to ethylene precursor 1-aminocyclopropane-1-carboxylic acid, ACC, and has been shown to induce ethylene generation in plants, Ferguson et al., "Stimulation of Ethylene Production in Bean Leaf Discs by the Pseudomonad phytotosin coronatine", Plant Physiol., Vol. 77, pp. 969 (1985). For coronatine preparation, Pst strains DC3000 and DC3661 were grown at 16° C. in Wooley's Medium. 1/15th volume of concentrated HCl was added to culture supernatant, which was then extracted with ethyl acetate. The organic phase was flash-evaporated at 45° C. and resuspended either in methanol for storage at −20° C. or in 1/40th original volume $H_2O$ for use in inoculations. Plants were inoculated by placing a 10 μl or 15 μl droplet on the leaf surface and then piercing the leaf with a syringe needle. Quantities of crude toxin preparation are presented as colony forming unit equivalents (cfu equivalents), relating unknown toxin concentration to the known quantity of original bacterial culture represented in a given toxin aliquot. Pure coronatine was prepared and stored in methanol; dried samples were resuspended in $H_2O$ immediately prior to use.

Toxin production plays a significant role in the virulence of bacterial plant pathogens. The relative absence of symptoms on ein2 plants infected with virulent Pst was tested to determine if it was due to a diminished response to coronatine. In the first set of experiments, crude toxin preparations were made from Pst DC3000. Tomato (Peto76) plants inoculated with the DC3000 toxin preparations showed the chlorotic response that is characteristic of coronatine treatment.

In contrast, Arabidopsis Col-0 leaves inoculated with the same preparations developed a strong purple hue in the region surrounding the inoculation site. This coloration was presumably due to increased anthocyanin production, a commonly observed stress response. The severity of the toxin response was dose-dependent over a 500 fold range of concentrations, with discoloration evident following applications of as little as $1\times10^7$ cfu equivalents of crude toxin. Purple coloration that extended down the petiole was observed using $5\times10^8$ cfu equivalents, and entire leaves frequently collapsed following application of $\geq 10^9$ cfu equivalents. Significantly, ein1-1, ein2-1 and eto1-1 plants exhibited responses to toxin treatment that closely resembled those seen in wild-type Col-0.

As a negative control in these experiments, preparations were also made from Pst DC3661. This strain is a tox derivative of DC3000 carrying a Tn5 insertion in a locus required for coronatine production. No response was observed in Arabidopsis or tomato leaves inoculated with DC3661 preparations.

A second set of experiments were performed using highly purified coronatine. Fifty ng of pure coronatine produced clearly observable responses of similar strength to those observed using approximately $5\times10^7$ cfu equivalents of crude preparation. Plant reactions to pure coronatine were very similar to those obtained with DC3000 toxin preparations: tomato leaves turned yellow, Arabidopsis leaves turned purple, symptoms were dose-dependent, and the responses of ein1-1, ein2-1 and eto1-1 plants were indistinguishable from those of Col-0.

Various modifications of the invention in addition to those shown and described herein will be apparent to those skilled in the art from the foregoing description. Such modifications are also intended to fall within the scope of the appended claims.

What is claimed:

1. A process for screening for a plant having disease tolerance comprising:
   (i) administering to a plant an inhibitory amount of gaseous ethylene,
   (ii) screening for ethylene insensitivity thereby producing ethylene insensitive plants,
   (iii) inoculating said ethylene insensitive plant with a pathogen wherein said pathogen is selected from the group consisting of Pseudomonas and Xanthomonas, and
   (iv) screening for disease tolerance; thereby identifying a disease tolerant plant.

2. A process for screening for a plant having disease tolerance comprising:
   (i) administering to a plant an inhibitory amount of gaseous ethylene,
   (ii) screening for an ethylene insensitive plant, said plant having root and stem elongation and increased ethylene production, thereby producing an ethylene insensitive plant;
   (iii) inoculating said ethylene insensitive plant with a pathogen, wherein said pathogen is a bacteria selected from the group consisting of Xanthomonas and Pseudomonas, and
   (iv) screening for a disease tolerance plant, thereby identifying a disease tolerant plant; said plant selected from the Family Cruciferae.

3. A process for screening for a plant having disease tolerance comprising:
   (i) administering to a plant an inhibitory amount of gaseous ethylene,
   (ii) screening for an ethylene insensitive plant, said plant having root and stem elongation and increased ethylene production, thereby producing an ethylene insensitive plant;
   (iii) inoculating said ethylene insensitive plant with a pathogen selected from the group consisting of Pseudomonas and Xanthomonas, and
   (iv) screening for disease tolerance, thereby identifying a disease tolerant plant; said plant selected from the group consisting of Family Cruciferae and Family Leguminosae.

4. A process for screening for a plant having disease tolerance comprising:
   (i) administering to a plant an inhibitory amount of gaseous ethylene,
   (ii) screening for an ethylene insensitive plant, said plant having root and stem elongation and increased ethylene production, thereby producing an ethylene insensitive plant;
   (iii) inoculating said ethylene insensitive plant with Pseudomonas, and
   (iv) screening for disease tolerance, thereby identifying a disease tolerant plant; said plant selected from the group consisting of Family Cruciferae and Family Leguminosae.

5. A process for screening for a plant having disease tolerance comprising:
   (i) administering to a plant an inhibitory amount of gaseous ethylene,
   (ii) screening for an ethylene insensitive plant, said plant having root and stem elongation and increased ethylene production, thereby producing an ethylene insensitive plant;
   (iii) inoculating said ethylene insensitive plant with a pathogen selected from the group consisting of *Pseudomonas syringae* and *Xanthomonas campestris*, and
   (iv) screening for disease tolerance, thereby identifying a disease tolerant plant; said plant selected from the group consisting of Family Cruciferae and Family Leguminosae.

6. A process for screening for a plant having disease tolerance comprising:
(i) administering to a plant an inhibitory amount of gaseous ethylene,
(ii) screening for an ethylene insensitive plant, said plant having root and stem elongation and increased ethylene production, thereby producing an ethylene insensitive plant;
(iii) inoculating said ethylene insensitive plant with a pathogen selected from the group consisting of *Pseudomonas syringae* and *Xanthomonas campestris*, and
(iv) screening for disease tolerance, thereby identifying a disease tolerant plant; said plant selected from the group consisting of Family Cruciferae, genus Arabidopsis, and Family Leguminosae, genus Glycine.

7. A process for screening for a plant having disease tolerance comprising:
(i) administering to a plant an inhibitory amount of gaseous ethylene,
(ii) screening for an ethylene insensitive plant, said plant having root and stem elongation and increased ethylene production, thereby producing an ethylene insensitive plant;
(iii) inoculating said ethylene insensitive plant with a pathogen selected from the group consisting of *Pseudomonas syringae* and *Xanthomonas campestris*, and
(iv) screening for disease tolerance, thereby identifying a disease tolerant plant; said plant selected from the group consisting of Family Cruciferae, genus Arabidopsis and genus Brassica, and Family Leguminosae, genus Glycine.

8. A process for screening for a plant having disease tolerance comprising:
(i) administering to a plant an inhibitory amount of gaseous ethylene,
(ii) screening for an ethylene insensitive plant, said plant having root and stem elongation and increased ethylene production, thereby producing an ethylene insensitive plant;
(iii) inoculating said ethylene insensitive plant with a pathogen selected from the group consisting of *Pseudomonas syringae*, and
(iv) screening for disease tolerance, thereby identifying a disease tolerant plant; said plant selected from the group consisting of Family Cruciferae and Family Leguminosae.

9. A process for screening for a plant having disease tolerance comprising:
(i) administering to a plant an inhibitory amount of gaseous ethylene,
(ii) screening for an ethylene insensitive plant, said plant having root and stem elongation and increased ethylene production, thereby producing an ethylene insensitive plant;
(iii) inoculating said ethylene insensitive plant with a pathogen selected from the group consisting of *Pseudomonas syringae*, and
(iv) screening for disease tolerance, thereby identifying a disease tolerant plant; said plant selected from the group consisting of Family Cruciferae genus Arabidopsis and Family Leguminosae genus Glycine.

10. A process for screening for a plant having disease tolerance comprising:
(i) administering to a plant an inhibitory amount of gaseous ethylene,
(ii) screening for an ethylene insensitive plant, said plant having root and stem elongation and increased ethylene production, thereby producing an ethylene insensitive plant;
(iii) inoculating said ethylene insensitive plant with a pathogen selected from the group consisting of *Pseudomonas syringae*, and
(iv) screening for disease tolerance, thereby identifying a disease tolerant plant; said plant selected from the group consisting of Family Cruciferae genus Arabidopsis and genus Brassica and Family Leguminosae genus Glycine.

11. A process for screening for a plant having disease tolerance comprising:
(i) administering to a plant an inhibitory amount of gaseous ethylene,
(ii) screening for an ethylene insensitive plant, said plant having root and stem elongation and increased ethylene production, thereby producing an ethylene insensitive plant;
(iii) inoculating said ethylene insensitive plant with Rhizoctonia, and
(iv) screening for disease tolerance, thereby identifying a disease tolerant plant; said plant selected from the group consisting of Family Cruciferae and Family Leguminosae.

12. A process for screening for a plant having disease tolerance comprising:
(i) administering to a plant an inhibitory amount of gaseous ethylene,
(ii) screening for an ethylene insensitive plant, said plant having root and stem elongation and increased ethylene production, thereby producing an ethylene insensitive plant;
(iii) inoculating said ethylene insensitive plant with *Rhizoctonia solani*, and
(iv) screening for disease tolerance, thereby identifying a disease tolerant plant; said plant selected from the group consisting of Family Cruciferae and Family Leguminosae.

13. A process for screening for a plant having disease tolerance comprising:
(i) administering to a plant an inhibitory amount of gaseous ethylene,
(ii) screening for an ethylene insensitive plant, said plant having root and stem elongation and increased ethylene production, thereby producing an ethylene insensitive plant;
(iii) inoculating said ethylene insensitive plant with Rhizoctonia, and
(iv) screening for disease tolerance, thereby identifying a disease tolerant plant; said plant selected from the group consisting of Family Cruciferae genus Arabidopsis and genus Brassica, and Family Leguminosae genus Glycine.

14. A process for screening for a plant having disease tolerance comprising:
(i) administering to a plant an inhibitory amount of gaseous ethylene,
(ii) screening for an ethylene insensitive plant, said plant having root and stem elongation and increased ethylene production, thereby producing an ethylene insensitive plant;

(iii) inoculating said ethylene insensitive plant with Rhizoctonia, and (iv) screening for disease tolerance, thereby identifying a disease tolerant plant; said plant selected from the group consisting of Family Leguminosae.

15. The process of claim 3 wherein said plant is selected from the Family Leguminosae genus Glycine.

16. The process of claim 3 wherein said pathogen is selected from the group consisting of *Pseudomonas syringae*.

17. The process of claim 3 wherein said pathogen is selected from the group consisting of *Pseudomonas syringae* and *Xanthomonas campestris*.

18. The process of claim 11 wherein said Rhizoctonia is *Rhizoctonia solani*.

19. The process of claim 13 wherein said Rhizoctonia is *Rhizoctonia solani*.

20. The process of claim 14 wherein said Rhizoctonia is *Rhizoctonia solani*.

21. A process for screening for a plant having disease tolerance comprising:
   (i) administering to a plant an inhibitory amount of gaseous ethylene,
   (ii) screening for an ethylene insensitive plant, said plant having root and stem elongation and increased ethylene production, thereby producing an ethylene insensitive plant;
   (iii) inoculating said ethylene insensitive plant with a pathogen selected from the group consisting of Pseudomonas, Xanthomonas, and Rhizoctonia;
   (iv) screening for disease tolerance, thereby identifying a disease tolerant plant.

* * * * *